United States Patent [19]

Mehta

[11] Patent Number: 4,709,041

[45] Date of Patent: Nov. 24, 1987

[54] 2-(FORMYLPHENYL) BENZOTRIAZOLE INTERMEDIATES

[75] Inventor: Avinash C. Mehta, Belmont, Mass.

[73] Assignee: Polaroid Corporation, Cambridge, Mass.

[21] Appl. No.: 900,238

[22] Filed: Aug. 25, 1986

Related U.S. Application Data

[63] Continuation of Ser. No. 321,588, Nov. 16, 1981, abandoned.

[51] Int. Cl.$^4$ ............................................. C07D 249/20
[52] U.S. Cl. ..................................... 548/260; 548/261; 524/91
[58] Field of Search .................... 548/260, 261; 524/91

[56] References Cited

U.S. PATENT DOCUMENTS

| | | | |
|---|---|---|---|
| 2,362,988 | 11/1940 | Conzetti et al. | 548/261 |
| 3,399,173 | 8/1968 | Heller et al. | 260/47 |
| 3,493,539 | 2/1970 | Skoultchi et al. | 548/261 |
| 4,041,044 | 8/1977 | White | 260/308 B |
| 4,119,634 | 10/1978 | Schoedet | 548/261 |
| 4,166,109 | 8/1979 | Jacquet et al. | 424/59 |
| 4,233,430 | 11/1980 | Jacquet et al. | 526/259 |

FOREIGN PATENT DOCUMENTS

| | | | |
|---|---|---|---|
| 0164138 | 12/1974 | Czechoslovakia | 548/261 |
| 2413005 | 10/1975 | Fed. Rep. of Germany | 548/261 |

OTHER PUBLICATIONS

Meislich, et al., *Schaum's Outline—Organic Chemistry*, McGraw-Hill, New York, 1977, pp. 288, 294–295.

Noller, Carl, *Textbook of Organic Chemistry*, W. B. Saunders, Philadelphia, (1966), p. 154.

McOmie, *Protective Groups in Organic Chemistry*, pp. 96, 97, 108, 109 and 115 (1970).

Locatelli, et al, "Degredation Unsaturated Polymers", *Chem. Abst.*, 78:59118h (1973).

Hora, et al., "Stable Color . . . Images", *Chem. Abst.*, 80:151,100 (1974).

McGinniss, Vincent, "Hardening Polymerizable Binders . . . ", Chem. Abst., 85:162043y (1976).

T. Norris et al., J. Chem. Soc., Chem. Commun., 1978, (21), 932–933.

S. Yoshida et al., Polymer Preprints, vol. 21, No. 1, Mar., 1980, p. 203.

*Primary Examiner*—Donald G. Daus
*Assistant Examiner*—Mark W. Noel
*Attorney, Agent, or Firm*—Louis G. Xiarhos

[57] ABSTRACT

Compounds of the formula

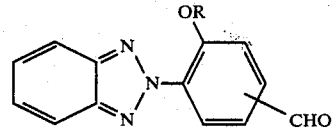

wherein R is hydrogen or a hydroxy-protecting group are disclosed. The compounds are versatile intermediates which can be derivatized by reaction of the formyl group to provide a wide variety of ultraviolet-absorbing substituted 2-(2-hydroxyphenyl)-2H-benzotriazoles.

10 Claims, No Drawings

2-(FORMYLPHENYL) BENZOTRIAZOLE INTERMEDIATES

This application is a continuation of copending application Ser. No. 321,588, filed Nov. 16, 1981, now abandoned.

BACKGROUND OF THE INVENTION

The present invention relates to novel chemical compounds and in particular to novel chemical compounds useful as intermediates in preparing a wide variety of substituted 2(2-hydroxyphenyl)-2H-benzotriazole compounds.

The use of phenyl -2H-benzotriazole compounds for the protection and stabilization of various materials against the action of ultraviolet radiation is well known. Especially useful compounds of this class are substituted 2-(2-hydroxyphenyl)-2H-benzotriazole compounds, i.e., compounds containing the moiety

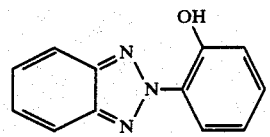

which moiety is substituted, on either the condensed phenyl ring or the 2-hydroxyphenyl ring, or both, with one or more substituent groups such as alkyl, alkoxy, aryl, aryloxy, or halogen. The substituent groups are generally employed to impart desired physical characteristics to the compound such as a desired solubility, substantivity, or compatibility with a substrate. Compounds comprising the 2-(2-hydroxyphenyl)-2H-benzotriazole moiety generally are capable of absorbing a high percentage of incident ultraviolet radiation and possess a high degree of stability to such radiation, such that they can provide substantial protection against ultraviolet radiation for extended periods of time. Certain of the substituted 2-(2-hydroxyphenyl)-2H-benzotriazoles have become commercially important and the preparation and utilization of such materials are of current widespread interest.

Substituted 2-(2-hydroxyphenyl)-2H-benzotriazole compounds, hereinafter referred to as substituted 2-HPB compounds, are normally prepared by diazotizing an o-nitroaniline, coupling the diazotized product with a phenol in a strong base, and subjecting the resultant 2-(2'-nitrophenylazo) phenol to reductive ring closure (triazolization). This method of preparation is well known and various methods of conducting same are described in a number of patents, e.g., U.S. Pat. Nos. 3,018,269; 3,230,194; 3,773,751; 4,041,044; and 4,230,967. The substituent groups on the condensed phenyl ring or 2-hydroxyphenyl ring are normally provided by use of appropriately substituted o-nitroaniline or phenol starting materials in the abovedescribed method of preparation This method of providing substituent groups is limiting in that appropriately substituted starting materials must be provided and the substituents are required to be stable to and compatible with the preparative reaction conditions. Thus, certain substituted 2-HPB compounds may not be capable of preparation by this method or may be prepared only in low yield or by resort to costly or complex process variations.

As an alternative means of providing desired substituted 2-HPB compounds, derivatization of an existing 2-HPB compound or protected 2-HPB compound may be considered. For example, certain derivatization reactions, directed toward production of certain polymerizable 2-HPB compounds, have been disclosed. The derivatization of 2-[(2-hydroxy-5-methyl)phenyl]-2H-benzotriazole with N-hydroxymethylacrylamide, N-hydroxymethyl- -phenylacrylamide, N-hydroxymethyl- -chloroacrylamide, and N-hydroxymethylmethacrylamide to produce polymerizable monomers wherein the acrylamido group is attached in the 3-phenyl position is disclosed in U.S. Pat. Nos. 3,399,173, 4,166,109 and 4,233,430 also disclose the derivatization of 2-[(2-hydroxy-5-methyl)phenyl]-2H-benzotriazole with N-hydroxymethylacrylamide. S. Yoshida and O. Vogl in Polymer Preprints, Vol. 21, No. 1, March 1980, p. 203, disclose a preparation of 2-[(2-hydroxy-5-vinyl)phenyl]-2H-benzotriazole by α-bromination of the ethyl group of 2-[(2-acetoxy-5-ethyl)phenyl]-2H-benzotriazole followed by dehydrobromination and hydrolysis of the acetoxy group to produce the desired monomer.

The present invention relates to novel compounds which are useful as intermediates in the preparation of ultraviolet-absorbing substituted 2-HPB compounds. The intermediates of this invention are capable of undergoing various types of derivatization reactions with a wide variety of derivatizing reactants so as to permit incorporation of a correspondingly wide variety of substituent groups into the 2-hydroxyphenyl ring of the 2-HPB moiety.

The compounds of this invention are aldehydes of the formula

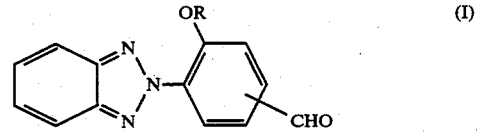

(I)

wherein R is hydrogen or a hydroxy-protecting group. The compounds may be referred to as 2-[(formyl-2-OR)phenyl]-2H-benzotriazoles.

The compounds of this invention are versatile intermediates in that the formyl group can, in general, undergo the numerous reactions of aromatic aldehyde functions and, thus, provides a reactive site at which a multiplicity of substituent groups can be appended to the 2-OR-phenyl ring.

In the compounds of this invention wherein R is hydrogen, derivatization of the formyl group can provide the desired substituted 2-HPB directly whereas if R is a hydroxyprotecting group it is necessary to both derivatize the formyl group and deblock the hydroxy group to provide the desired substituted 2-HPB. Thus, when R is hydrogen, the desired substituted 2-HPB may be provided by a single reaction involving appropriate derivatization of the formyl group. When R is a hydroxy-protecting group, derivatization of the formyl group will, in general, provide a blocked or protected product derivative which is then deblocked to provide the desired substituted 2-HPB.

It should be understood that preparation of the desired substituted 2-HPB may require a multi-step synthesis in which derivatization of the formyl group is the first step and the resultant derivative is further reacted to provide the desired product. The later reactions will generally involve treatment of the substituent group provided by the derivatization reaction to convert same to the substituent group ultimately desired. Where R is a hydroxy-protecting group, the deblocking reaction may be conducted at any suitable point in the synthetic sequence.

For certain reactions, the use of compounds of this invention wherein R is a hydroxy-protecting group will be preferred. The hydroxy-protecting group may provide any of a number of functions such as preventing unintended reaction of the hydroxy group, providing favorable inductive effects so as to increase the reactivity of the formyl group or decrease the reactivity of unsubstituted sites on the 2-OR-phenyl ring, or allowing more facile isolation of a reaction product, e.g., by imparting desired solubility characteristics to the product. The hydroxy-protecting group may provide such functionality during preparation of the instant compounds or in conjunction with reaction of the formyl group or of derivatives formed by such reaction.

Various hydroxy-protecting groups are well known in the art and may be used in the compounds of this invention. Suitable groups are those capable of removal under acidic, neutral, or basic conditions so as to regenerate the hydroxy group. Inasmuch as the hydroxy-protecting group is intended to be removed from a derivative of a compound of this invention, it should be capable of removal under conditions appropriate for the derivative. Thus, if a particular derivative is insoluble or unstable in acidic media, a hydroxy-protecting group capable of removal under neutral or basic conditions will generally be preferred. Additional considerations regarding the choice of a particular hydroxyprotecting group can include the ease with which a compound of this invention can be prepared to comprise a given protecting group, the degree of difficulty associated with removal of the protecting group, and the ability of the protecting group to perform any of the above-noted functions. Among the various hydroxy-protecting groups which may be used in the compounds of this invention, specific mention may be made of lower alkyl having 1 to 6 carbon atoms such as methyl, ethyl, isopropyl, and tert-butyl; methoxymethyl; methylthiomethyl; phenacyl; p-bromophenacyl; 2-tetrahydrofuranyl; 2-tetrahydropyranyl; ethoxycarbonyl; 2,2,2-trichloroethoxycarbonyl; and acyl, e.g., acetyl and benzoyl.

As indicated by formula (I), the formyl group can be substituted at any of the available positions on the 2-OR-phenyl ring. Preferably, the formyl group is substituted at the 5-position such that the compound is of the formula

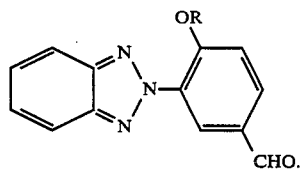 (II)

Compounds of formula (II) are preferred from a synthetic standpoint in that they may be prepared by methods, described herein, which employ the commercially available 2-[(2-hydroxy-5-methyl)phenyl]-2H-benzotriazole as a starting material. In addition, positioning of the formyl group at the 5- position is preferred insofar as it facilitates formation or reaction of the formyl group due to minimized steric interference from the benzotriazole moiety or the —OR group.

Preferred compounds of this invention of formula (II) include the following:

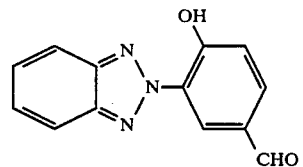

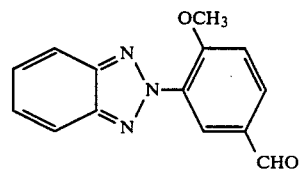

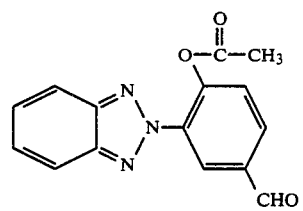

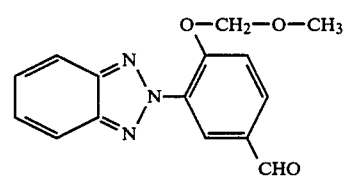

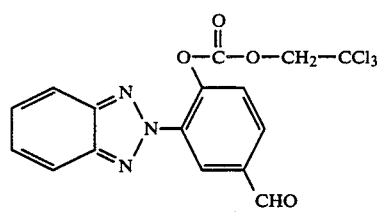

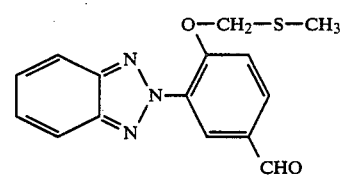

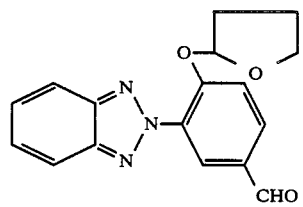

-continued

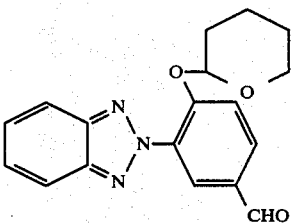

The compounds of this invention can be prepared by converting the halomethyl group of a 2-[(halomethyl-2-OR¹phenyl]-2H-benzotriazole to a formyl group in accordance with the reaction (1):

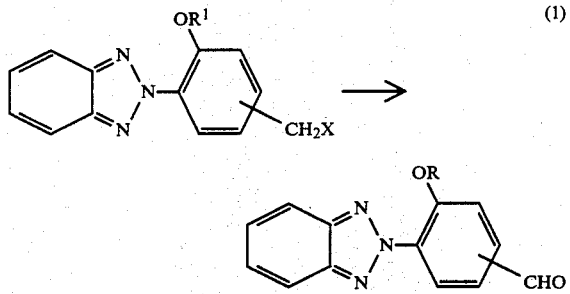

wherein X is chloro or bromo, R¹ is a hydroxy-protecting group, and R is as previously defined. The reaction may be conducted using well known reactants and procedures for effecting conversion of alkyl halide groups to a formyl group. Thus, the halomethyl compound shown above can be converted to the desired formyl compound by reaction with an aromatic N-oxide such as pyridine N-oxide, α-picolinium N-oxide, or quinoline N-oxide followed by treatment of the thus-formed product with base as described, for example, by W. Feely et al., J. Org. Chem., 22, 1135(1957) or V. J. Traynelis et al., J. Org. Chem., 40:16, 2365 (1975); by reaction with dimethylsulfoxide followed by treatment of the thus-formed product with base as described, for example, by N. Kornblum et al., J. Am. Chem. Soc., 81, 4113 (1959) or H.R. Nace et al., J. Org. Chem., 24, 1792 (1959); or by reaction with hexamethylene tetramine as described, for example, by S. J. Angyal et al., J. Chem. Soc., 2700 (1949) or S. J. Angyal, Org. React., 8, 197 (1954).

The hydroxy-protecting group R¹ can be any of the groups also suitable for use as the hydroxy-protecting group R. With reference to reaction (1), those R¹ groups stable to the conditions of the reaction will be maintained intact during the reaction and R in the final product and R¹ will be the same. However, certain of the hydroxy-protecting groups which can be used in the compounds of this invention, and as R¹, such as acyl, ethoxycarbonyl, and 2,2,2-trichloroethoxycarbonyl, undergo hydrolysis in the presence of aqueous base or aqueous acid. Thus, the use of aqueous acid or base in the above-mentioned reactions may result in hydrolysis of such R¹ protecting groups. The resultant product is a compound of this invention wherein R is hydrogen. If it is desired to minimize or prevent hydrolysis during the above-mentioned base treatment steps, an appropriate base may be used under anhydrous conditions, e.g., sodium bicarbonate, sodium hydride, or triethylamine in an anhydrous solvent such as acetonitrile. If the hydroxy-protecting group is hydrolyzed, but a protecting group is desired in the final product, the resultant hydroxy compound can be reacted according to conventional procedures to "reblock" the hydroxy group.

Illustrative preparations are shown in the following reaction schemes employing 2-[(2-acetoxy-5-bromomethyl)phenyl]-2H-benzotriazole and 2-[(2-methoxy-5-bromomethyl)phenyl]-2H-benzotriazole as starting materials and α-picolinium N-oxide and aqueous hydroxide anion as reagents. In reaction scheme (1a), the acetyl protecting group is illustrated as being hydrolyzed by the aqueous hydroxide and reintroduced by the known procedure of blocking the hydroxy group with acetic anhydride in the presence of a catalytic amount of triethylamine. The following reaction schemes are illustrative only and not intended to be of limiting effect:

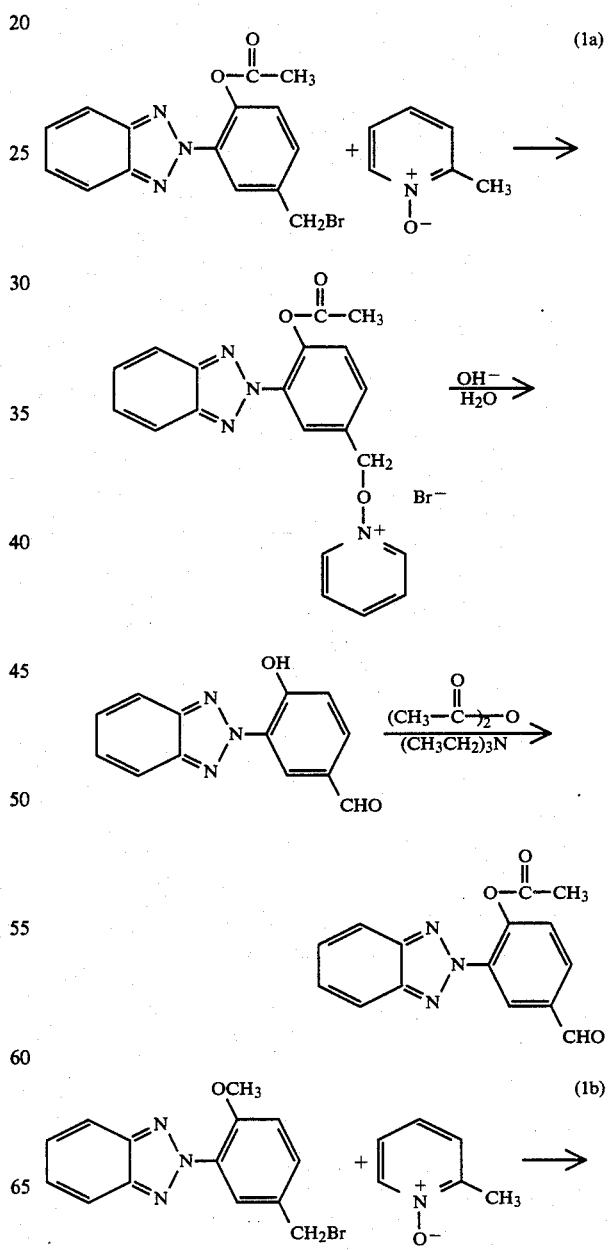

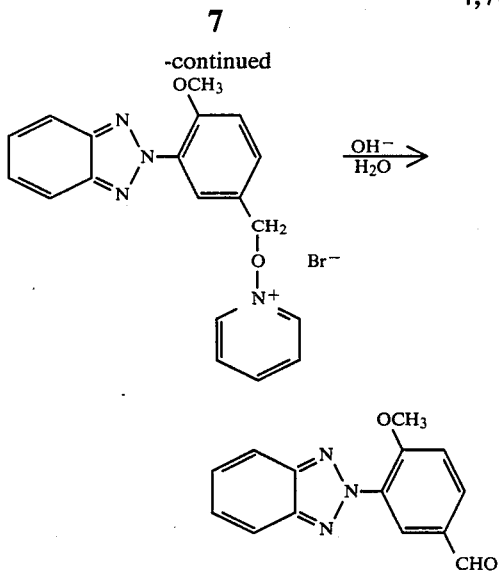

In a preferred method of preparation, the compounds of this invention are prepared by hydrolysis of the dihalomethyl group of a 2-[(dihalomethyl-2-OR¹)phenyl]-2H-benzotriazole in accordance with the reaction (2):

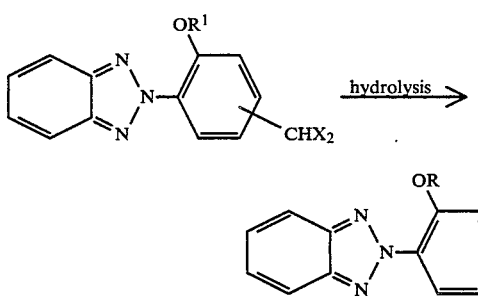

wherein X, R, and R¹ are as previously defined. Various methods for hydrolyzing benzal halides to the corresponding aldehydes are known and any suitable method may be used to prepare the compounds of this invention. Thus, the dihalomethyl compound shown above may be hydrolyzed to the desired formyl compound by reaction with sodium carbonate as described, for example, by J. J. Brown et al., Can. J. Chem., 33, 1819 (1955); by reaction with aqueous silver nitrate in methyl cellosolve as described, for example, by H. Gilman et al., J. Am. Chem. Soc., 78, 1689 (1956); by reaction with sodium formate in aqueous alcohol as described, for example, by E. Eliel, et al., J. Chem. Soc., 1628 (1955); or by reaction with sodium acetate in acetic acid as described, for example, by W. Reid et al., Chem. Ber., 91, 2479 (1958). In a preferred method, the hydrolysis is carried out by reacting the dihalomethyl starting material with an alkali metal acetate, such as sodium acetate, in an aqueous alcohol solution, preferably aqueous methanol, and treating the resultant product mixture with hydrochloric acid. The starting material is believed to react with both the acetate and alcohol to effect displacement of both halide atoms and production of a mixture of products which are then hydrolyzed directly to the desired aldehyde compound by the hydrochloric acid. As indicated by Example 4 herein, this preferred method provides the compounds of this invention in high yield and good purity.

As with the preparative method illustrated above by reaction (1), the hydroxy-protecting group R¹ in the starting material for reaction (2) can be any of the groups also suitable for use as the hydroxy-protecting group R. With regard to the preferred method of conducting the hydrolysis, wherein aqueous hydrochloric acid is employed, those R¹ groups possessing sufficient stability in the presence of this acid will be maintained intact during the reaction and R in the final product and R¹ will be the same. However, certain of the hydroxy-protecting groups which can be used as R¹, such as acyl, ethoxycarbonyl, and 2,2,2-trichloroethoxycarbonyl, may undergo at least partial hydrolysis in the presence of the aqueous hydrochloric acid with resultant formation of a compound of this invention wherein R is hydrogen. As indicated above in regard to reaction (1), such a compound can be "reblocked" by conventional procedures of blocking phenolic hydroxy groups.

Illustrative preparations are shown in the following reaction schemes employing 2-[(2-acetoxy-5-dibromomethyl)phenyl]-2H-benzotriazole and 2-[(2-methoxy-5-dibromomethyl)phenyl]-2H-benzotriazole as starting materials and sodium acetate, methanol, and hydrochloric acid as reagents. In reaction scheme (2a), the acetyl group is illustrated as being hydrolyzed by the hydrochloric acid and then reintroduced in the previously described manner. The following reaction schemes are illustrative only and not intended to be of limiting effect:

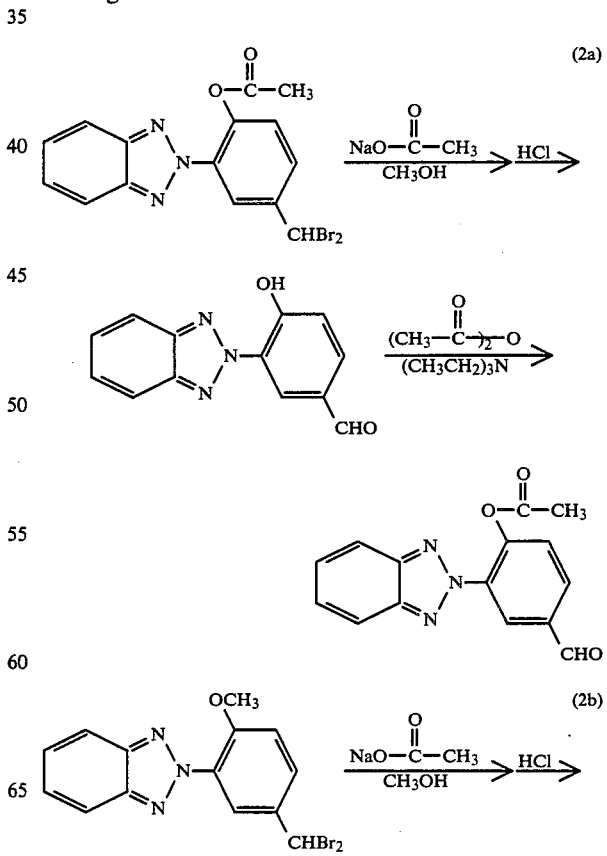

-continued

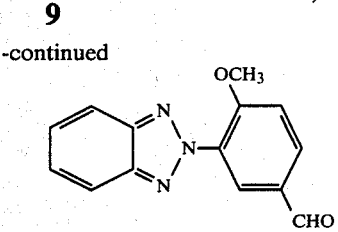

With regard to the reblocking of the hydroxy group of the compound

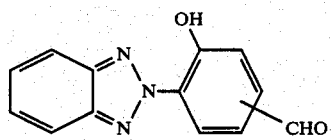

it should be noted that various methods of blocking hydroxy groups with removable protecting groups are well known. Any of the known methods may be employed provided that there is not an unacceptable accompanying side reaction of the formyl group. Methods which may be employed include methylation with dimethylsulfate; acylation with acetic anhydride in the presence of a basic catalyst; methoxymethylation as described, for example, by Kaoru Fuji et al., Synthesis, 4, pp. 276–277 (1975); tetrahydrofuranylation as described, for example, by C. G. Kruse et al., Tetrahedron Lett., 20, p. 1725 (1976); tetrahydropyranylation as described, for example, by W. F. Parham et al., J. Am. Chem. Soc.,70, pp. 4187–4189 (1948); and trichloroethoxycarbonylation as described, for example, by Just et al., Synthesis, p. 457, (1976).

The 2-[(halomethyl and dihalomethyl-2-OR$^1$)phenyl]-2H-benzotriazoles used as starting materials in the above preparative methods and a method of preparing same constitute the subject matter of the copending U.S. patent application Ser. No. 321,589 of A. C. Mehta, filed of even date. In accordance with the disclosure therein, the halomethyl and dihalomethyl compounds can be prepared by blocking the hydroxy group of a 2-[(methyl-2-hydroxy)phenyl]-2H-benzotriazole with a hydroxy-protecting group to form the corresponding 2-[(methyl-2-OR$^1$)- phenyl]-2H-benzotriazole wherein R$^1$ is the hydroxy-protecting group and reacting the 2-[(methyl-2-OR$^1$)-phenyl]-2H-benzotriazole with a benzylic chlorinating or brominating agent to form the corresponding 2-[(halomethyl or dihalomethyl-2-OR$^1$)phenyl]-2H-benzotriazole. With regard to this method of preparation, the relative molar amount of benzylic chlorinating or brominating agent will generally determine whether the halomethyl or dihalomethyl species is provided.

In general, those procedures commonly used in the art for removal of hydroxy-protecting groups can be used in deblocking the hydroxy group in derivatives obtained by reaction of the compounds of this invention. The deblocking may be conducted under acidic, neutral, or basic conditions as appropriate for the derivative and as appropriate for a given protecting group. Protecting groups capable of removal under acidic conditions, e.g., alkyl, tetrahydrofuranyl, tetrahydropyranyl, and phenacyl can be removed in the presence of, for example, mineral acids such as hydrobromic acid or in the presence of boron tribromide. Protecting groups capable of removal under basic conditions, e.g., acyl, ethoxycarbonyl, and 2,2,2-trichloroethoxycarbonyl can be removed in the presence of, for example, aqueous alkali hydroxides such as aqueous sodium hydroxide or potassium hydroxide so as to generate a hydroxy anion moiety which can be protonated by treatment with acid.

Reactions which can be undergone by the compounds of this invention include nucleophilic addition, oxidation, reduction, and condensation reactions. The substituents incorporated into the compound by these and other reactions of the formyl group can be used to impart desired physical or chemical properties to the compound such as a desired solubility, substantivity, diffusivity, compatibility with a substrate, or chemical reactivity. An exemplary application is the provision of a substituent group rendering the compound non-diffusible. Such a group may be provided by reacting a compound of this invention with a long chain alkyl amine to form the corresponding Schiff base followed by reduction of the —C=N—bond. The compound may also be rendered non-diffusible by attachment to a polymer backbone, e.g., by reaction with polyvinyl alcohol to form the polymeric acetal.

Although the present intermediates have been described in reference to reaction of the formyl group with a derivatizing reagent to effect conversion of the formyl group to another substituent moiety, it will be appreciated that the reactivity of the formyl group can be used to append the 2-HPB moiety to a relatively large molecule or material and that such a reaction may be more aptly characterized as substitution or incorporation of the 2-HPB moiety onto or into the larger molecule.

Compounds of this invention wherein R is hydrogen are, of course, in the 2-HPB class of compounds and may accordingly be used as UV-absorbing compounds of that class. Generally, however, such compounds will be employed as reactive intermediates, as described herein.

The following examples are provided to further illustrate the present invention. The specific limitations set forth in the following examples are intended as illustrative and not limitative.

EXAMPLE 1

60.0 grams of 2-[(2-hydroxy-5-methyl)phenyl]-2H-benzotriazole, available from Ciba-Geigy Corp. under the tradename Tinuvin P, were suspended in 180 ml. of acetic anhydride and 2 ml. of concentrated sulfuric acid were added with moderate agitation. An exotherm occurred and a homogeneous solution resulted. The solution was allowed to stand for one hour at ambient temperature and then heated on a steam bath for one hour, cooled to room temperature, and poured into ice-water with stirring, resulting in formation of a white solid. After stirring for 1.5 hours, the white solid was isolated by filtration, washed with cold water, and dried in a vacuum oven. Yield of 71.2 g. of 2-[(2-acetoxy-5-methyl)phenyl]-2H-benzotriazole as a white solid having a melting point of 104°–106° C. Proton nuclear magnetic resonance and infrared spectral data confirmed the structure.

EXAMPLE 2

A mixture of 14.7 g. of 2-[(2-acetoxy-5-methyl)-phenyl]-2H-benzotriazole, prepared as described in Example 1, 8.9 g. of N-bromosuccinimide, and 0.5 g. of benzoyl peroxide in 150 ml. of carbon tetrachloride were refluxed for 12 hours. The reaction mixture was then cooled to ambient temperature and insolubles removed by filtration. The filtrate was washed with cold water and then with brine and dried over anhydrous sodium sulfate. The solvent was then removed on a rotary evaporator to yield 18.5 g. of a solid which was recrystallized from a 5:1 by volume mixture of hexane:methylene chloride. Yield of 7.5 g. of 2-[(2-acetoxy-5-bromomethyl)phenyl]-2H-benzotriazole, melting point 126°–128° C. Proton nuclear magnetic resonance and infrared spectral data confirmed the structure.

EXAMPLE 3

A mixture of 10.7 g. of 2-[(2-acetoxy-5-methyl)-phenyl]-2H-benzotriazole, prepared as described in Example 1, 15.0 g. of N-bromosuccinimide, and 0.8 g. of benzoyl peroxide in 125 ml. of carbon tetrachloride was refluxed for 12 hours. The reaction mixture was then cooled to ambient temperature and insolubles removed by filtration. The filtrate was washed with cold water and dried over anhydrous sodium sulfate. The solvent was then removed on a rotary evaporator to yield 22.9 g. of solid which was recrystallized from isopropyl alcohol. Yield of 16.5 g. of 2-[(2-acetoxy-5-dibromomethyl)phenyl]-2H-benzotriazole, melting point 140°–142° C. Proton nuclear magnetic resonance spectral data confirmed the structure.

EXAMPLE 4

A mixture of 4.25 g. of 2-[(2-acetoxy-5-dibromomethyl) phenyl]-2H-benzotriazole, 4.25 g. of sodium acetate trihydrate, 40 ml. of methanol, and 20 ml. of water was heated at reflux for 6 hours. 20 ml. of concentrated hydrochloric acid were then added and refluxing continued an additional 3 hours. The reaction mixture was cooled in an ice bath and the resultant precipitate was isolated by filtration, washed with water and dried in a vacuum oven. Yield of 2.14 g. of 2-[(2-hydroxy-5-formyl)phenyl]-2H-benzotriazole, melting point 170°–172° C. Proton nuclear magnetic resonance analysis confirmed the structure.

What is claimed is:

1. A compound of the formula

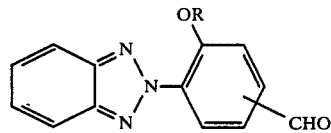

wherein R is hydrogen or a hydroxy-protecting group capable of removal so as to regenerate the hydroxy group.

2. A compound of claim 1 wherein R is a hydroxy protecting group selected from the group consisting of lower alkyl having 1 to 6 carbon atoms; methoxymethyl; methylthiomethyl; phenacyl; p-bromophenacyl; 2-tetrahydrofuranyl; 2-tetrahydropyranyl; ethoxycarbonyl; 2,2,2-trichloroethoxycarbonyl; and acyl.

3. A compound of claim 2 wherein R is acyl.

4. A compound of claim 3 wherein R is acetyl.

5. A compound of claim 1 wherein R is hydrogen.

6. A compound of claim 1 of the formula

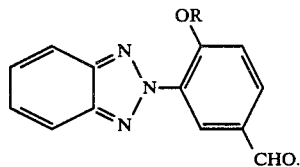

7. A compound of claim 6 wherein R is a hydroxy protecting group selected from the group consisting of lower alkyl having 1 to 6 carbon atoms; methoxymethyl; methylthiomethyl; phenacyl; p-bromophenacyl; 2-tetrahydrofuranyl; 2-tetrahydropyranyl; ethoxycarbonyl; 2,2,2-trichloroethoxycarbonyl; and acyl.

8. A compound of claim 7 wherein R is acyl.

9. A compound of claim 8 wherein R is acetyl.

10. A compound of claim 6 wherein R is hydrogen.